United States Patent
Gorsen

(10) Patent No.: US 7,493,663 B2
(45) Date of Patent: Feb. 24, 2009

(54) PROTECTIVE AND THERAPEUTIC BODY GEAR

(76) Inventor: Robert M. Gorsen, 6514 W. Langley La., McLean, VA (US) 22101

( * ) Notice: Subject to any disclaimer, the term of this patent is extended or adjusted under 35 U.S.C. 154(b) by 11 days.

(21) Appl. No.: 11/756,804

(22) Filed: Jun. 1, 2007

(65) Prior Publication Data

US 2007/0281568 A1 Dec. 6, 2007

Related U.S. Application Data

(60) Provisional application No. 60/810,267, filed on Jun. 2, 2006.

(51) Int. Cl.
- A42C 1/06 (2006.01)
- A42C 5/04 (2006.01)
- A41D 31/02 (2006.01)
- A41D 27/28 (2006.01)

(52) U.S. Cl. .......... 2/410; 2/455; 2/411; 2/171.2; 2/184.5

(58) Field of Classification Search .......... 2/455, 2/456, 410, 6.8, 411, 414, 425, 16, 22, 24, 2/61, 162, 170, 171.2, 171.8, 181, 200.1, 2/231, 232, 241, 268, 267, 272, 909–911, 2/917–920, DIG. 5, DIG. 11
See application file for complete search history.

(56) References Cited

U.S. PATENT DOCUMENTS

| | | | |
|---|---|---|---|
| 2,218,947 A | 10/1940 | Brunzell | |
| 2,996,724 A | 8/1961 | Rose et al. | |
| 3,929,135 A * | 12/1975 | Thompson | 604/385.08 |
| 4,581,773 A | 4/1986 | Cunnane | |
| 4,996,724 A | 3/1991 | Dextrase | |
| 5,226,180 A | 7/1993 | Leach | |
| 5,289,591 A | 3/1994 | Andersen | |
| 5,365,607 A * | 11/1994 | Benevento, Jr. et al. | 2/181.4 |
| 5,461,730 A | 10/1995 | Carrington | |
| 5,481,759 A | 1/1996 | Rinaldi | |
| 5,926,849 A | 7/1999 | Boyle | |
| 6,009,555 A | 1/2000 | Siprut | |
| 6,125,645 A * | 10/2000 | Horn | 62/259.3 |
| 6,162,960 A * | 12/2000 | Klein | 602/41 |
| 6,563,013 B1 * | 5/2003 | Murota | 604/380 |
| 6,966,071 B1 | 11/2005 | Cascone | |
| 2005/0175269 A1 * | 8/2005 | Ashton et al. | 385/1 |
| 2005/0214501 A1 * | 9/2005 | Baychar | 428/90 |
| 2006/0069380 A1 * | 3/2006 | Chen et al. | 604/391 |

OTHER PUBLICATIONS www.haloheadband.com; Halo Headbands (4 pages).
www.underarmour.com; UA Performance Headband; Padded Elbow Sleeve (2 pages).
www.full90.com; F90 Premier headgear; ForceField Protective Headband (2 pages).
Waterproof/breathable fabric description (2 pages).
Capillary action description (2 pages).

* cited by examiner

Primary Examiner—Bobby H Muromoto, Jr.
(74) Attorney, Agent, or Firm—Schnader Harrison Segal & Lewis, LLP

(57) ABSTRACT

A moisture absorbing and impact protective material comprising a layer of impact protection material forming a gutter, a layer of absorbent material disposed adjacent to the impact protection material at least in part within the gutter, and a layer of moisture transport material disposed at least in part external to the impact protection material gutter and having an interface with the absorbent material. The moisture transport material wicks away moisture from a wearer and transports it to the absorbent material. Excess moisture accumulates in the gutter.

20 Claims, 5 Drawing Sheets

PROTECTIVE AND THERAPEUTIC BODY GEAR

PRIORITY CLAIM

The present application claims priority to U.S. Provisional Application 60/810,267, entitled "Protective and Therapeutic Body Gear", filed Jun. 2, 2006. The provisional application is hereby incorporated in its entirety.

FIELD OF INVENTION

This invention relates to protective body gear that is formed from impact protection and moisture absorption materials.

BACKGROUND OF THE INVENTION

Impact protection devices are needed to safeguard individuals such as sports participants, military personnel and others engaging in high risk activities. Traditionally, openings have been required in impact protective material for it to be breathable. Even with openings present the remainder of the material can create a hot, moist interface with the wearer. The presence of such openings can also compromise the level of protection such materials can offer. Moisture absorbent material has been used in combination with impact absorbing material to reduce the moisture problem. This has only been successful to a limited extent, in part because the moisture absorbing material becomes saturated and the moisture remains in contact with the wearer. Accordingly, there is a need for a protective device that performs moisture control and impact protection functions.

SUMMARY OF THE INVENTION

Embodiments of the present invention provide a protective device that is effective in removing moisture that arises from impact absorbing material used therein. The device has a layer of absorbent material disposed adjacent to an impact protection material. A layer of moisture transport material is disposed adjacent to the impact protection material and on the side of the impact protection material opposite the absorbent material. A gutter is formed of the impact material to facilitate moisture transport and removal from the wearer.

Embodiments of the present invention provide moisture-absorbing and impact-protective material comprising a layer of impact protection material, a layer of absorbent material disposed adjacent to the impact protection material; and a layer moisture transport material disposed adjacent to the impact protection material and on the side of the impact protection material opposite the absorbent material. In one embodiment, the layers are fastened to one another. In a preferred embodiment, at least the impact material is folded so as to for a gutter between the layers of the absorbent material.

The combination of materials may be used to make a variety of items, including headbands, wristbands, neckbands, armbands, and guards for the knees, shins and elbows. In further embodiment of the invention, the material inventive arrangement is formed into eye shields, head bands or a cap which accommodate a cold pack, hot pack, vibration devices or other therapeutic device.

DESCRIPTION OF THE DRAWINGS

The invention is best understood from the following detailed description when read with the accompanying drawings.

DETAILED DESCRIPTION OF THE INVENTION

Figure 1:
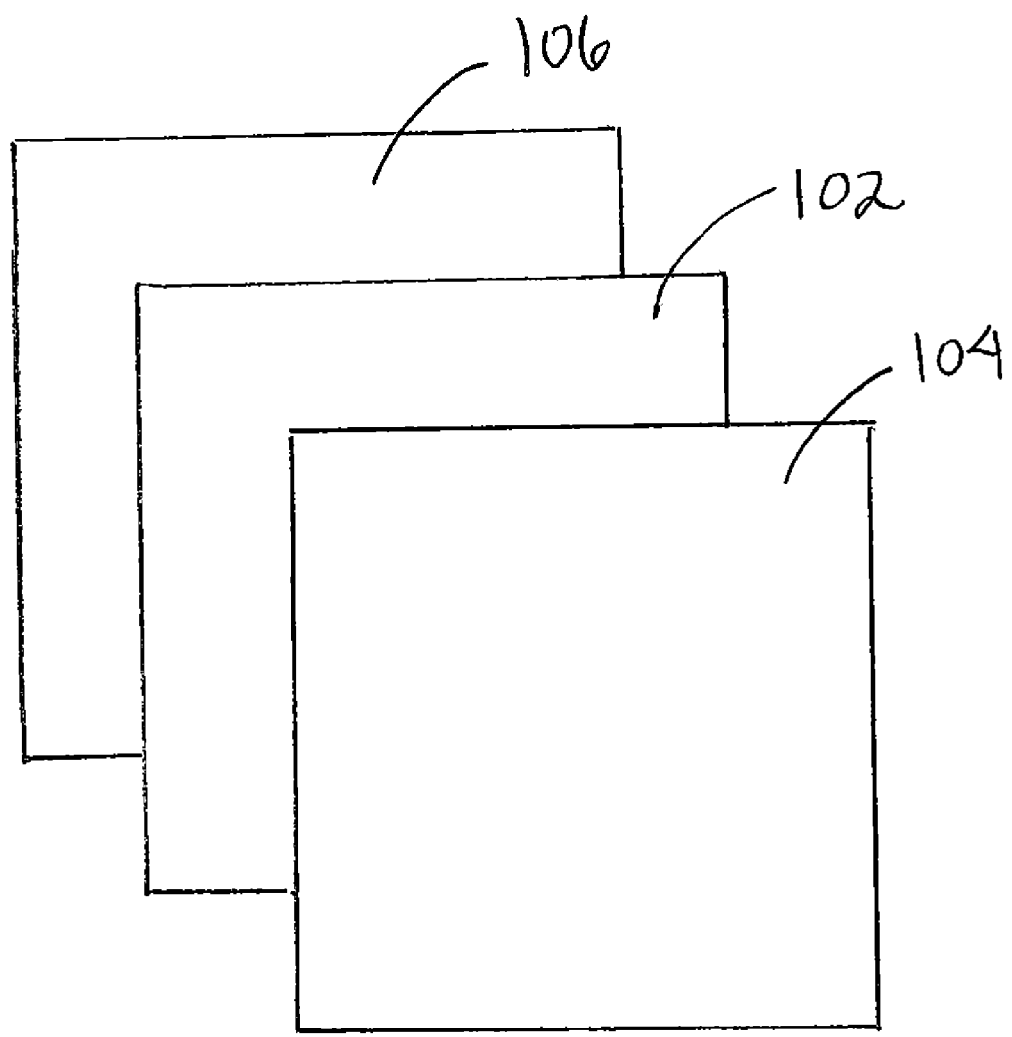
FIG. 1 depicts an exploded view of a novel combination of materials according to an illustrative embodiment of the invention.

FIG. 1 depicts an exploded view of a novel combination of materials for use in a protective garment according to an illustrative embodiment of the invention. An impact protection material 102 is dispose between a layer of absorbent material 104 and moisture transport material 106. The layers may be stitched to one another or fastened by other means. It is also possible for one or more of the layers to be bonded to one another.

Figure 2:
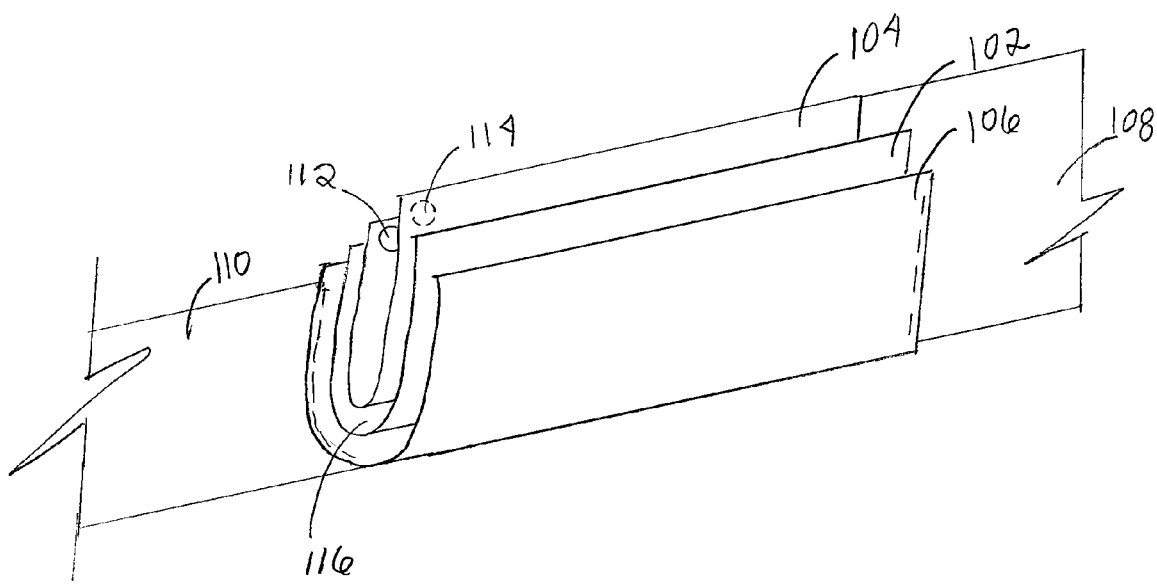
FIG. 2 depicts an exploded view of a protective garment according to an illustrative embodiment of the invention.

FIG. 2 depicts an exploded view of the protective article of FIG. 1 in a folded configuration. This is the preferred configuration for use of the article. Impact protection material 102 forms a u or v-shape within absorbent material 104, preferably disposed on the inside of the fold and moisture transport material 106 preferably disposed on the outside. FIG. 2 shows moisture transport material 106 fully surrounding impact protection material 102, however, it is within the spirit and scope of the invention to extend around impact protection material 102 to a lesser extent. It is preferable to have moisture transport material protect the wearer from direct contact with certain types of impact protection material 102. The exterior face of the layered material can be any desired material, including but not limited to the moisture transport material 106 as shown in FIG. 2.

Impact protection material 102 forms a gutter 116 to retain liquid absorbed and transported by absorbent material 104 and moisture transport material 106. A mechanism 108, 110 for the protective garment to be secured to a user is also provided. It is noted that the article can be folded in the reverse direction and still exhibit some or all of the benefits as when folded with the absorbent material in the interior of the fold. These benefits will be described in more detail below.

Figure 3:
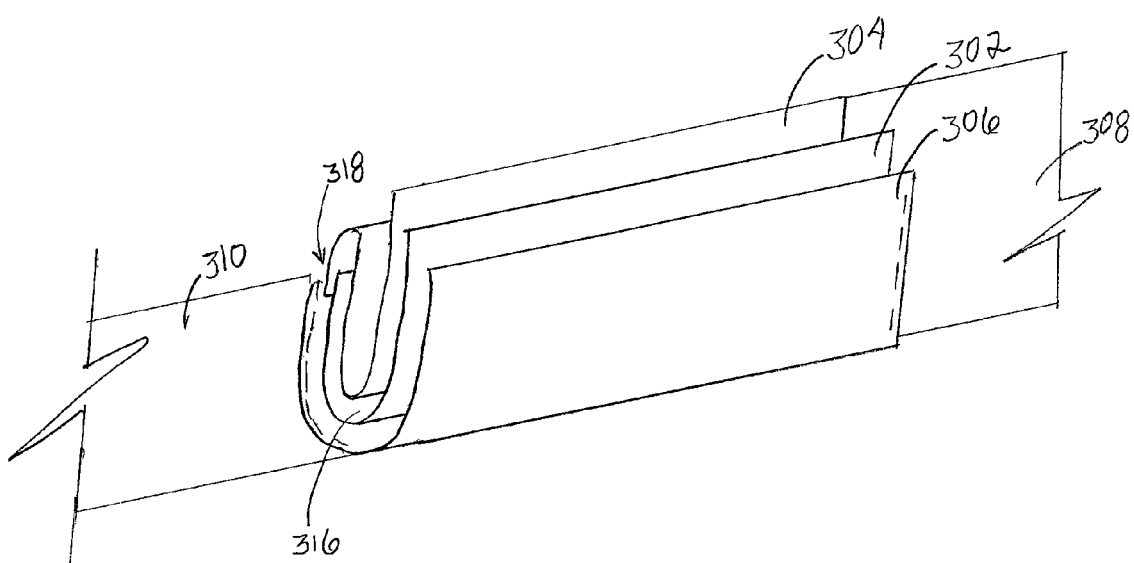
FIG. 3 depicts an exploded view of a protective garment according to a further illustrative embodiment of the invention.

FIG. 3 depicts an exploded view of a further illustrative embodiment of the invention. In this embodiment the impact material 302 forms a gutter 316. Absorbent material 304 is disposed within impact material gutter 316, forming a u or v-shape therein. Absorbent material 304 extends out of the gutter and between impact protection material 302 and moisture transport material 306. The interface 318 of absorbent material 304 and moisture transport material 306 can extend be any amount that allows the transfer of moisture to absorbent material 304.

Figure 4:
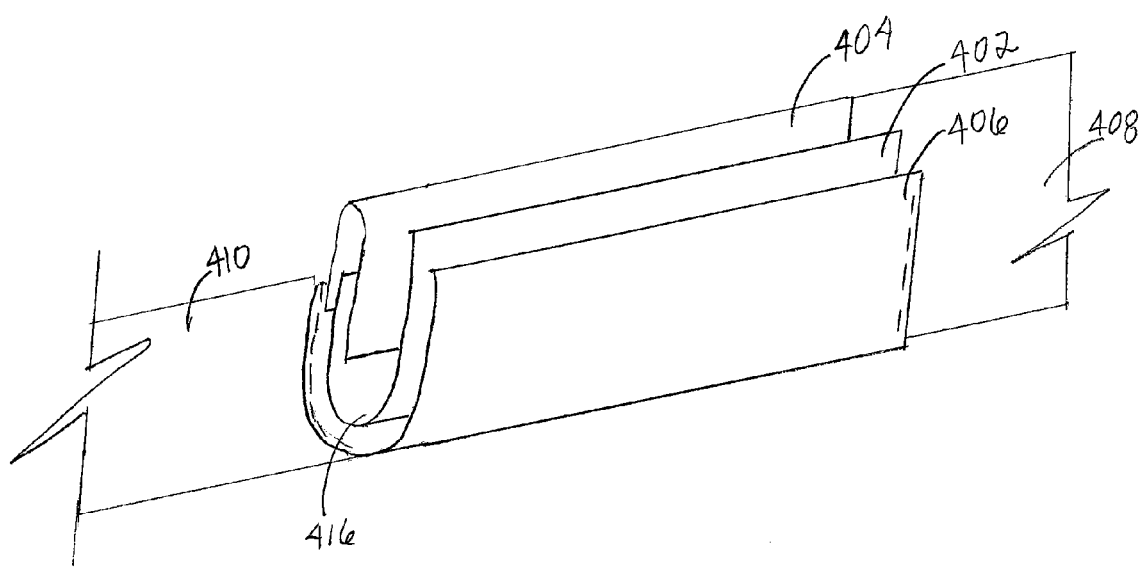
FIG. 4 depicts an exploded view of a protective garment according to yet a further illustrative embodiment of the invention.

FIG. 4 depicts an exploded view of yet another illustrative embodiment of the invention. In this embodiment, absorbent material 404 extends into impact protection material 402, but is not folded to follow the contour of gutter 416. Absorbent layer 404 can extend to any length within gutter 416, provided that it can carry moisture toward the gutter, and as discussed above, to various lengths between moisture transport material 406 and impact protection material 402.

Figure 5:
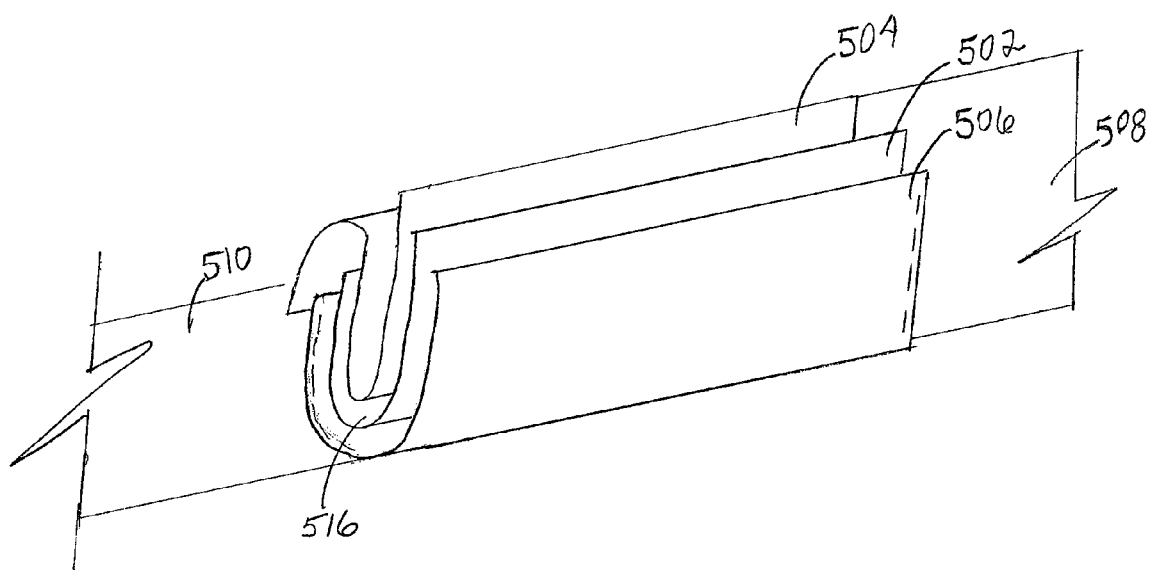
FIG. 5 depicts an exploded view of a protective garment according to another illustrative embodiment of the invention.

FIG. 5 depicts an exploded view of another illustrative embodiment of the invention. In this embodiment absorbent material 504 extends within impact protection material 502 to allow moisture to collect in gutter 516 if necessary. Absorbent material 504 overlaps moisture transport material 506 on its outside face or edge. This overlap or interface can extend any amount over moisture transport material 506, but is likely effective enough extending only a minimum amount over the edge.

It is noted that combinations of features shown in, and described with respect to FIGS. 1-5 are within the spirit and scope of the invention.

The novel system provides impact protection and moisture control in a single product. Traditional technology requires an impact protective material to have some form of openings to render the material breathable. This can compromise the protective benefits of the material and add additional manufacturing expense. The novel system combines an impact protective material with a moisture absorbent layer and a moisture transport material to direct moisture away from the skin. The impact protection material may or may not have openings.

The moisture transport material creates a capillary action that transports moisture toward the absorbent material. If the absorbent material becomes saturated, the gutter formed by the u or v-shaped impact protection material acts as a reservoir to inhibit moisture dripping onto the wearer. An article made of the layered material and folded as shown in FIG. 2 is positioned on the user so the fold is at the lowest position of the article. For example, a wrist band is worn with the gutter toward the hand and a headband is worn with the gutter toward the brow. It is noted that the absorbent material need not be a folded length of material. The same or similar effect can be achieved if it is a single layer in the interior of a folded length of the material combination. Furthermore, it need not extend completely to the bottom of the gutter, but can extend to any length therein.

In an illustrative embodiment of the invention, a component to maintain the article in a folded position is included. For example, as shown in FIG. 2, a hook material piece 112 is placed at a first position on the article and a loop material piece 114 is placed at a second position, so the article can be folded to create the gutter and maintained in the folded position. Other folding components may be used such as snaps and buttons.

The order of materials can be varied, however, it has been determined that having the moisture transport material against the user is most effective for moisture control. It is also possible to have either the impact protection layer as single, rather than a folded layer, but the gutter effect would be sacrificed.

Various materials can be used to provide the desired characteristics of each layer of the protective article. The impact protection material may be for example, an open cell foam such as polyethylene bubble foam. Other synthetic materials may also be used, such as neoprene. Natural rubber materials are another option for the impact protection layer.

The absorbent material layer is preferably a terry cloth or similar material. Cotton or cotton-containing materials in general are an excellent choice for the absorbent layer. The absorbent layer may also exhibit a capillary effect along the material, rather than through it. This can facilitate the transfer of moisture into the gutter.

The moisture transport layer can be any material in which a capillary effect can be created through the material. Wicking materials such as those made by Under Armor®, Adidas®, Nike® and Gortex® are suitable in addition to other types/brands. Gortex®, for example has a porous fluoropolymer membrane with a urethane coating bonded to a fabric such as nylon or polyester. The membrane has approximately nine billion pores per square inch, making them permeable to water vapor but not liquid water. Generally, a material that blocks liquid water but lets water vapor pass through is suitable for the moisture transport layer. This allows moisture generated by the wearer to pass through to the absorbent layer, but will not let liquid water vapor pass back to the wearer when the absorbent material becomes saturated. Wicking materials can enhance the moisture control of the article by wicking moisture away from the user while drawing moisture toward the absorbent layer through the capillary effect.

The construction of the layered material can affect the moisture control ability of the article. The moisture transported by the moisture transport material must reach the absorbent material for the article to be effective. Accordingly, an interface should exist between the two materials. The interface can be to any extent and need not be face to face. Therefore, overlap of one material on another and the type of seam used can have a bearing on the effectiveness of the article. The moisture transport material can overlap the absorbent material, such that the moisture transport material folds over the edge of the absorbent material, thereby facilitating the absorbent material's absorption of moisture wicked away from the wearer by the moisture transport layer. The materials may be permanently attached to one another or separable to facilitate cleaning and/or allow interchangeability of components.

FIG. 2 shows a securing or fastening mechanism to secure the article to a wearer as pieces of material 108, 110 extending from moisture transport material 106. Material 108, 110 may be or have attached to it a hook and loop material such as Velcro®. A section of hook material may be attached to one end of the protective garment and a section of a loop material may be attached to opposite end such that joining of at least a portion of the sections of hook and loop materials secures the protective garment to the body area. The securing mechanism may also be an elastic material attached to the garment such that the garment forms a stretchable loop that can be disposed around a body section. The securing mechanism may take on many forms and may be attached to the layered material in many ways and at different points. Both adjustable and fixed size securing mechanism can be incorporated into the article. The mechanism may extend from the ends of the layered material component or be incorporated into the ends. Other fastening mechanisms include for example snaps and lengths of material that can be tied.

The protective system may be used to form many different articles. Examples of use include, a headband, neckband, wristband, armband, knee or ankle support, and shin guard.

The layered material can also be used for therapeutic purposes. For example, migraine sufferers may use the system in the form of a headband or cap that can hold cold packs to their head. Eye shields can be incorporated into the article to help with light sensitivity. The layered material may also be used to hold other therapeutic devices to a user such as hot packs and vibration devices. A band soaked in cold water could be a cooling device. In an illustrative embodiment of the invention, an article comprising the layered material has an attachment component to attach a therapeutic device. This may be for example, a pocket or a fastening device.

While the invention has been described by illustrative embodiments, additional advantages and modifications will occur to those skilled in the art. Therefore, the invention in its broader aspects is not limited to specific details shown and described herein. Modifications, for example, types of material and configurations of articles made with material may be made without departing from the spirit and scope of the invention. Accordingly, it is intended that the invention not be limited to the specific illustrative embodiments, but be interpreted within the full spirit and scope of the appended claims and their equivalents.

The invention claimed is:

1. A protective article comprising:
   a layer of impact protection material folded to form a gutter to retain liquid;
   a layer of absorbent material disposed adjacent to the impact protection material at least in part within the gutter; and
   a layer of moisture transport material disposed at least in part external to the impact protection material gutter and having an interface with the absorbent material
   wherein the article is configured such that the opening of the gutter is not disposed toward a surface of a wearer on which the protective article is disposed: and
   wherein the absorbent material layer and the impact protection material layer are different layers.

2. The protective article of claim 1 wherein the impact protection material is an open cell foam.

3. The protective article of claim 1 wherein the absorbent material contains cotton.

4. The protective article of claim 1 wherein the moisture transport material is a wicking material.

5. The protective article of claim 1 further comprising a securing mechanism.

6. The protective article of claim 1 wherein the article is a headband.

7. The protective article of claim 1 wherein the article is a wristband.

8. The protective article of claim 1 wherein the article is a neckband.

9. The protective article of claim 1 wherein the article is an armband.

10. The protective article of claim 1 wherein the article is a shin guard.

11. The protective article of claim 1 further comprising an eye shield.

12. The protective article of claim 1 further comprising a therapeutic device incorporation mechanism.

13. The protective article of claim 1 further comprising a folding component to maintain the article in a position in which the gutter is formed.

14. The protective article of claim 1 further comprising material attached to the article to form a complete cap.

15. The protective article of claim 1 wherein the moisture transport material is disposed on the external part of the gutter facing a wearer.

16. The protective article of claim 15 wherein the moisture transport material is further disposed on the external part of the gutter facing away from the wearer.

17. The protective article of claim 1 wherein the absorbent material is further disposed external to the gutter.

18. The protective article of claim 17 wherein the absorbent material is disposed between the impact protection material and the moisture transport material.

19. A method of manufacturing a protective article comprising:
    providing a layer of impact protection material;
    folding the layer of impact protection material to form a gutter to retain liquid:
    providing a layer of absorbent material disposed adjacent to the impact protection material;
    providing a layer of moisture transport material disposed adjacent to the impact protection material and on the side of the impact protection material opposite the absorbent material;
    fastening the moisture transport material, absorbent material and impact protection material together;
    configuring the article such that the opening of the gutter is not disposed toward a surface of a wearer on which the protective article is disposed; and
    wherein the absorbent material layer and the impact protection material layer are different layers.

20. A method of protecting a body section comprising:
    providing a layer of impact protection material;
    folding the layer of impact protection material to form a gutter to retain liquid;
    providing a layer of absorbent material disposed adjacent to the impact protection material;
    providing a layer of moisture transport material disposed adjacent to the impact protection material and on the side of the impact protection material opposite the absorbent material;
    securing the combination of the moisture transport material, absorbent material and impact protection material to a body section.

* * * * *